United States Patent [19]
Amos et al.

[11] 3,967,109
[45] June 29, 1976

[54] AUTOMATIC FOCUSING SYSTEM

[75] Inventors: Lynn G. Amos, Raleigh; Jerry S. Boone, Garner, both of N.C.

[73] Assignee: Corning Glass Works, Corning, N.Y.

[22] Filed: Jan. 23, 1975

[21] Appl. No.: 543,515

Related U.S. Application Data

[62] Division of Ser. No. 399,619, Sept. 21, 1973, abandoned.

[52] U.S. Cl. ............................... 250/201; 250/235; 250/216
[51] Int. Cl.² ............................................ G01J 1/20
[58] Field of Search ............ 250/571, 578, 234–236, 250/216, 559, 201, 204, 222 PC; 356/39, 40; 354/25, 195; 353/101; 178/DIG. 29

[56] References Cited
UNITED STATES PATENTS

| | | | |
|---|---|---|---|
| 2,850,239 | 9/1958 | Polanti et al. | 250/222 PC X |
| 3,351,744 | 11/1967 | Masterson | 250/569 X |
| 3,493,764 | 2/1970 | Craig | 353/101 X |
| 3,532,045 | 10/1970 | Genahr | 354/25 |
| 3,610,934 | 10/1971 | Turner | 250/235 X |
| 3,622,797 | 11/1971 | Bragg | 250/234 |
| 3,670,153 | 6/1972 | Rempert et al. | 250/234 X |
| 3,708,619 | 1/1973 | Martin | 353/101 X |
| 3,883,689 | 5/1975 | Mansour et al. | 178/DIG. 29 |

*Primary Examiner*—Walter Stolwein
*Attorney, Agent, or Firm*—Walter S. Zebrowski; Clarence R. Patty, Jr.

[57] ABSTRACT

In a system which automatically analyzes laboratory slides, the adjustable objective lens is automatically focused. A beam splitter splits light from the slide into two parts. One slide image is projected to an actual image plane where it is converted into electrical signals representing the optical characteristics of the slide. The other slide image is projected to a parfocal image plane at which two light sensing devices for the focusing system are positioned. One light sensing device is in front of the parfocal image plane and the other is behind the parfocal image plane. These light sensing devices produce electrical signals representing the position of the actual image plane with respect to the desired image plane. The electric signals are differentiated and then applied to a comparator which supplies pulses to a stepping motor which moves the objective lens. The coupling between the stepping motor and the objective lens includes an eccentric member which translates the objective lens with no sliding friction. This allows very accurate positioning of the objective lens.

10 Claims, 7 Drawing Figures

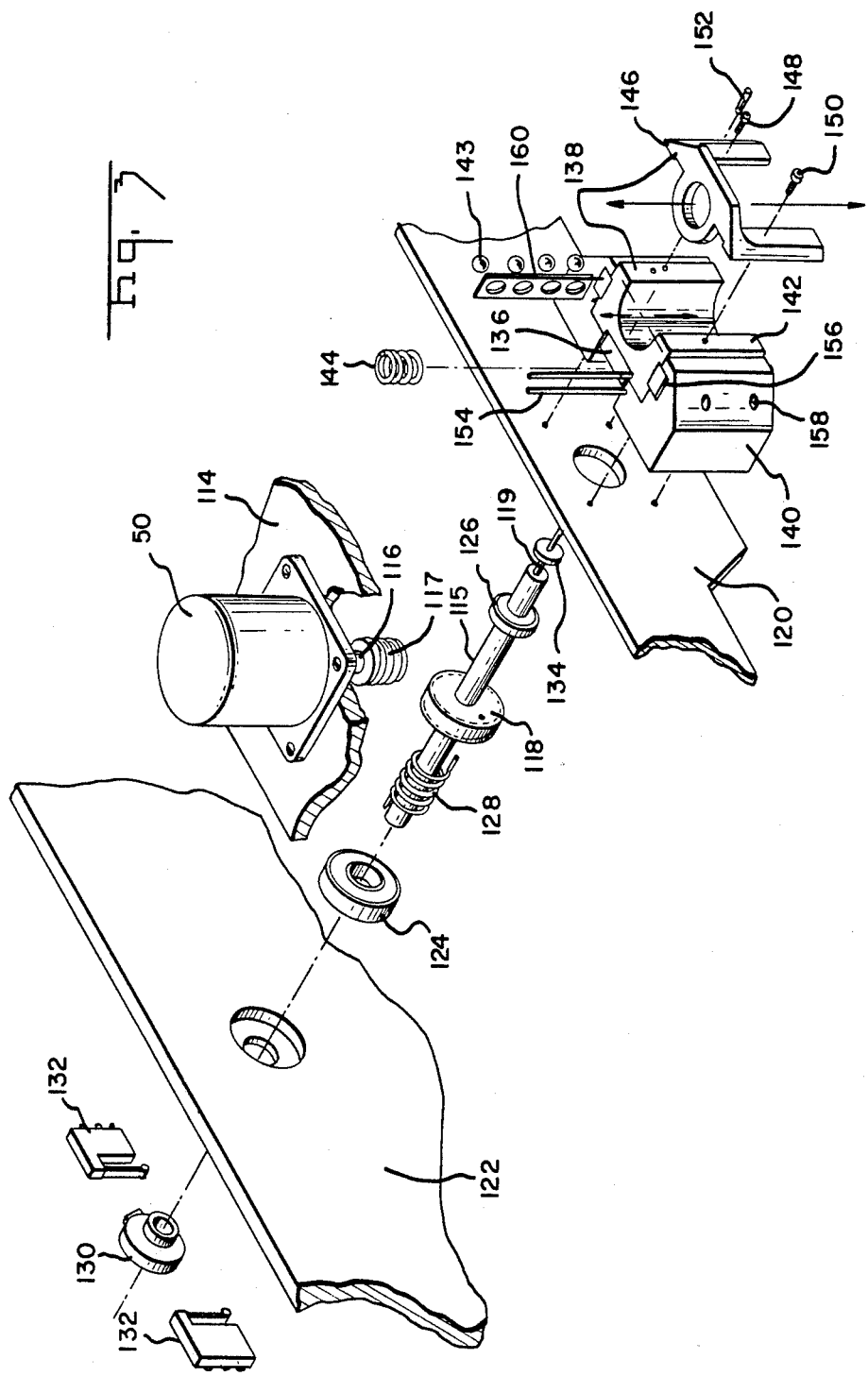

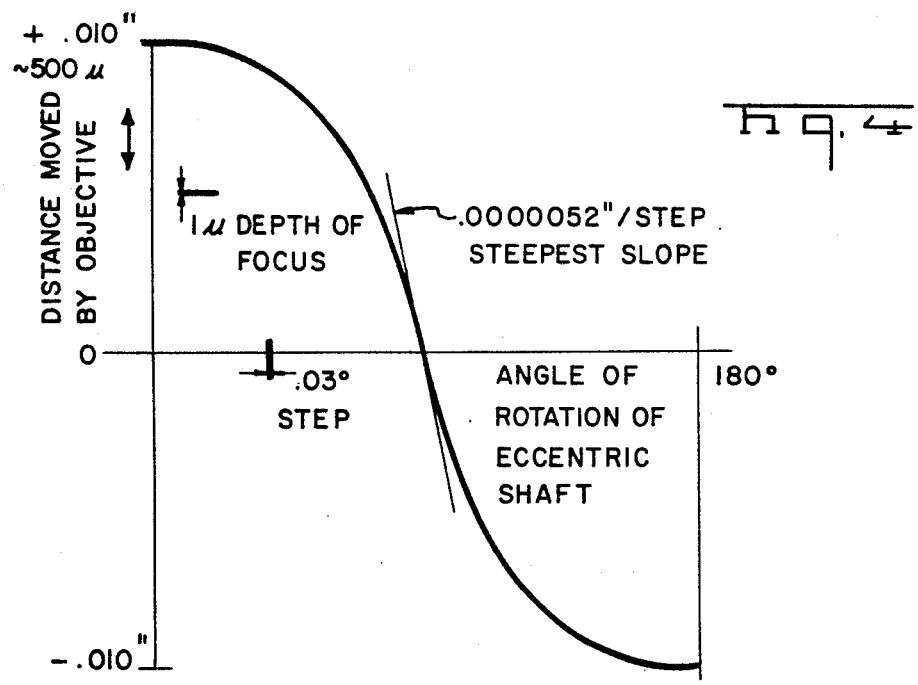
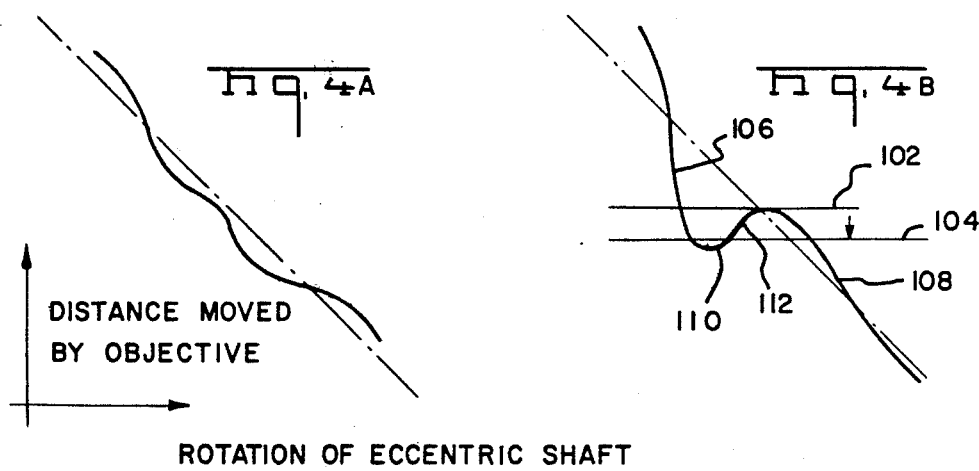

AUTOMATIC FOCUSING SYSTEM

This application is a divisional application of Ser. No. 399,619, filed Sept. 21, 1973, now abandoned.

BACKGROUND OF THE INVENTION

This invention relates to apparatus for converting the optical image of a laboratory slide to electrical signals and more particularly to an automatic focusing system for such apparatus.

In the analysis of blood samples, the blood is smeared on a laboratory slide and the smear is stained. By counting the different kinds of leukocytes on the stained smear, laboratory technicians perform what is referred to as a white blood cell differential. Automation of this differential has significant economic impact because the differential is performed so frequently at every hospital. A thesis by J. W. Bacus, "An Automated Classification of the Peripheral Blood Leukocytes by Means of Digital Image Processing," University of Illinois, Chicago, 1971, describes one automated system.

In a system developed by my co-employees, a scanning unit (in this case a T.V. camera) linearly sweeps a vidicon target subjected to intense illumination which passes through the smeared slide. Such a system is described in copending application Ser. No. 353,004, filed Apr. 20, 1973 now U.S. Pat. No. 3,883,852.

In such a system the light passing through the slide is focused by an objective lens. It is desirable to bring this image into focus on the television type converter.

SUMMARY OF THE INVENTION

In accordance with this invention an automatic focusing system is controlled by electrical signals produced by light sensing devices positioned in front of and behind a parfocal image plane.

A beam splitter projects two images of the slide. One image is focused on the converter. The other image is projected to the parfocal image plane. A rotating mirror successively scans the slide image across the light sensing devices positioned in front of and behind the parfocal image plane.

In one embodiment of this invention the masks in front of the light sensing devices are adjustable so that the two light sensing devices scan the same portion of the slide image. A second beam splitter further splits the parfocal image into two parts. One part is projected to a light sensing device in front of the parfocal image plane. The other part is projected to a light sensing device behind the parfocal image plane. Reflected images of the two masks are projected back through the second beam splitter to a microscope. The operator can adjust the positions of the two masks so that their image coincide in the microscope. In this manner an adjustment can be made so that the same portion of the slide image is scanned across both light sensing devices.

In accordance with another important aspect of this invention the mechanism which adjusts the position of the objective lens is accurate and effective to move the objective lens in very small increments. This is accomplished by using a stepping motor which actuates an eccentric bearing through an anti-backlash worm and worm wheel arrangement. The objective lens is constrained for translatory movement in roller bearings. The roller bearings and the worm and worm wheel arrangement allow ultra-small increments of motion to be imparted to the adjustable objective which can be lifted free and cannot be driven into the slide.

The foregoing and other objects, features and advantages of the invention will be better understood from the following more detailed description and appended claims.

DESCRIPTION OF THE DRAWINGS

FIG. 3 shows the focusing mechanism;
FIG. 4 depicts the translatory motion of the objective lens as a function of shaft angle of the stepping motor;
FIG. 4A is an enlargement of a portion of the plot of FIG. 4;
and
FIG. 4B is a similar enlargement depicting undesirable motion.

DESCRIPTION OF THE PREFERRED EMBODIMENT

Figure 1:
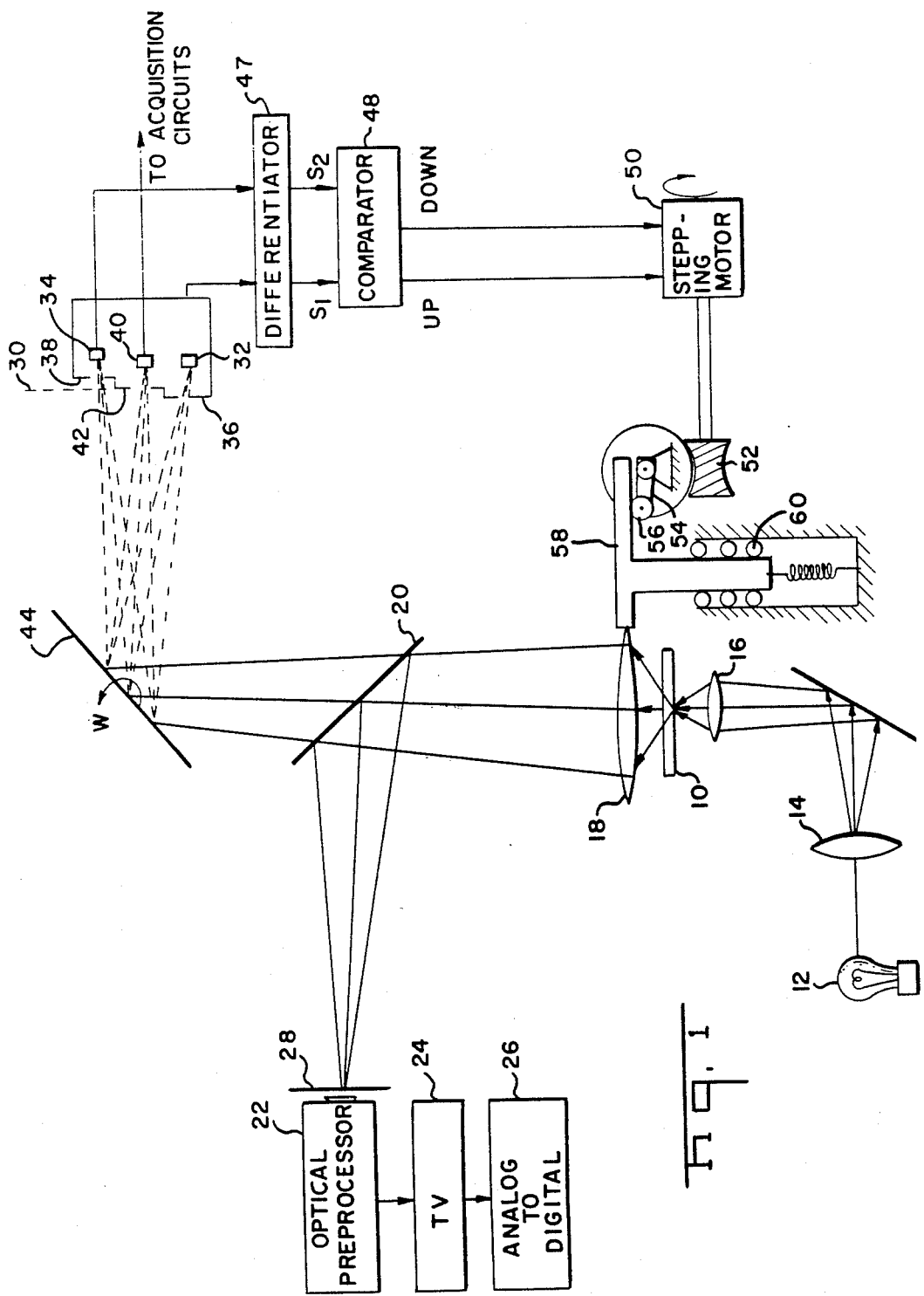
FIG. 1 depicts the automatic focusing system of this invention.

FIG. 1 shows the optics for a system for scanning and counting leukocytes on a blood smeared slide 10. Light from the lamp 12 passes through condenser lenses 14 and 16 and through the slide 10. The light is collected by the adjustable objective lens 18 and passes through a first beam splitter 20. This first beam splitter transmits approximately 40% of the light to the automatic focus and acquisition system of which this invention is a part. The remainder of the light is directed to the optical preprocessor 22 which applies it to the television type detector 24. The analog-to-digital converter 26 produces an electrical output in the form of digital signals representing the optical characteristics of the blood smeared slide 10. These digital signals are used to automatically classify and count the blood cells on the slide.

The objective lens 18 focuses the slide image at a desired image plane which is coincident with the actual image plane 28 when the slide image is in focus. It is desirable to keep the image focused at the plane 28 for the best conversion of the image to an electrical output. In order to do this, the other portion of the light from the first beam splitter 20 is projected to a parfocal desired image plane 30. First and second light sensing devices 32 and 34 are respectively positioned to receive light from in front of and behind the parfocal image plane 30. The mask 36 is positioned in front of the parfocal image plane so that light from the slide image is projected through an aperture in the mask onto the first light sensing device 32. A mask 38 is positioned behind the parfocal image plane 30 so that light from the slide image passes through an aperture in the mask onto the second light sensing device 34.

A third light sensing device 40 has a mask 42 which is positioned at the parfocal image plane 30. The light sensing device 40 produces an electrical signal which is used in the acquisition circuitry which is described in the copending application Ser. No. 400,915, filed Sep. 26, 1973, Adkins. The light sensing devices may be photomultipliers as an example.

A rotating mirror 44 scans the slide image across the masks. As the image is deflected across the masks, the electrical signals from the light sensing devices provide a measure of light to dark (or dark to light) transitions in the image. These electrical signals are applied to differentiator 47 and to comparator 48.

The signal $S_1$ is the signal from the light sensing device 32 which gathers light from in front of the parfocal image plane 30. The signal $S_2$ is from the light sensing device 34 which gathers light from in back of the parfocal image plane. These signals are differentiated to emphasized the high-frequency components of the waveform. When the actual image plane coincides with the desired image plane, the images at the sensing devices 32 and 34 are equal and slightly blurred and edges in the image are soft. Consequently, the signals $S_1$ and $S_2$ have relatively long rise and fall times and the amplitudes of the differentiated signals are relatively low. If the image plane moves from the desired image plane, the image becomes more in focus at one sensor and less at the other. The edges in the images become sharper at the sensor with the better focus and softer at the other; consequently the amplitude of the differentiated signal increases from the sensor with the better focus and decreases from the other. Therefore, the differentiated signals specify the direction in which the objective lens 18 is to be moved to bring the image into focus at the desired image plane. The comparator 48 controls logic which supplies pulses to the stepping motor 50. When the differentiated signal $S_1$ is greater than differentiated signal $S_2$ the comparator supplies pulses to the stepping motor which moves the objective lens up. When differentiated signal $S_2$ is greater than differentiated signal $S_1$, pulses are supplied to the stepping motor 50 to move it in the opposite direction.

The mechanism which moves the objective lens 18 upwardly or downwardly is extremely precise. It includes a spring loaded worm gear 52 driven by the stepping motor 50. The worm gear rotates an eccentric member 54. This member has a roller bearing 56 which bears against a protrusion 58 on the objective lens holder. The objective lens holder is constrained for translatory motion by the roller bearings 60.

Figure 2:
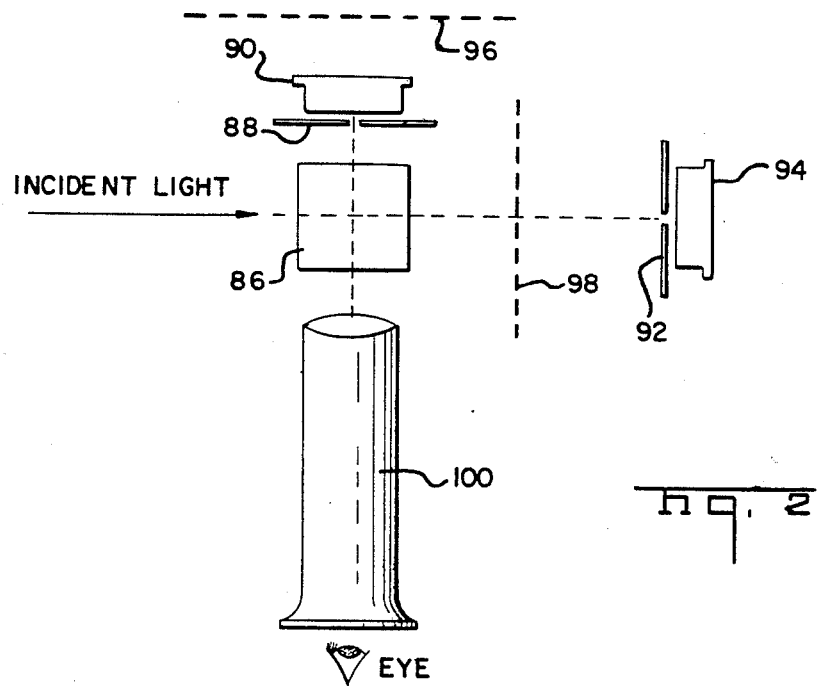
FIG. 2 shows a modification.
Figure 2A:
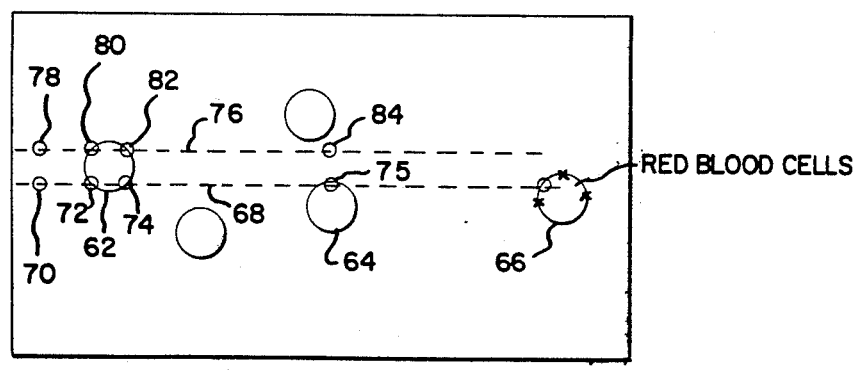
FIG. 2A depicts the scanning of the slide image.

The modification of FIG. 2 avoids the problem of the light sensing devices receiving light from different portions of the slide image. This problem can be better understood with reference to FIG. 2A. FIG. 2A depicts the slide image with the blood cells 62, 64 and 66 therein. As the mirror 44 rotates the light sensor 32 receives light from the cricled portions of the slide image which lie along the dashed line 68. That is, light sensing device 32 receives light from the portion 70, then 72, then 74 ... then 75 and so on. Simultaneously, the light sensing device 34 receives light from the circled portions of the slide image which lie along the dashed line 76. That is, it successively receives light from the circled portions 78, 80, 82 ... 84.

When light sensing devices 32 and 34 are respectively receiving light from the portions 70 and 78, a true indication of focus is obtained because these two portions of the image are approximately the same. Similarly, the portion 72 is similar to the portion 80 and the portion 74 is similar to the portion 82. However, at the point in time when the light sensing device 32 is receiving light from the portion 75 while the light sensing device 34 is receiving light from the portion 84, the light sensing devices will not produce electrical signals indicating a true focus. Since the portion 75 lies in a blood cell, the light supplied to the device 32 is very much less than the light supplied to the device 34 but this is not necessarily caused by a lack of focus.

The arrangement of FIG. 2 overcomes this problem.

Incident light from the rotating mirror 44 is applied to a second beam splitter 86. The incident light is split with half going to the assembly which includes aperture 88 and sensor 90 and the other half going to the assembly which includes mask 92 and light sensing device 94. The two images from the beam splitter 86 each have a desired parfocal image plane. The light mask 80 is in front of the desired parfocal image plane 96 and the mask 92 is behind the desired parfocal image plane 98.

The masks 88 and 92 are adjustable. Alternatively, only one of the masks can be adjustable in position with respect to the other. The mask 92 is adjustable up and down. The mask is also adjustable in directions transverse to the plane of the drawing showing the mask.

In order to adjust the apertures so that they intercept light from the same portion of the slide image, a low power microscope 100 is provided. The beam splitter 86 is a 50–50 beam splitter so that light reflected from the mask assemblies goes back into the beam splitter and is projected into the low power microscope 100. The observer looking into the microscope sees superimposed images of the apertures in the two masks. (Only one or the other will be in focus at a given time.) Alignment of the masks is accomplished by moving one of the masks until the apertures coincide in the superimposed images.

The mechanism connecting the stepping motor 50 to the objective lens holder is shown in FIG. 3. The requirement for such a precise mechanism can best be explained with reference to FIGS. 4, 4A and 4B. FIG. 4 depicts the rotation of the eccentric shaft through 180°. Translatory motion of the objective lens holder is shown as the ordinate. The stepping motor rotates in 1.8° steps. The worm gear reduction causes the eccentric shaft to rotate through 180° in 0.03° steps. Each step of the stepping motor causes a translatory motion of the objective holder. The distance traversed is a sine function of the eccentric shaft position. The greatest movement is .0000052 in. when the eccentric shaft is at midrange. Elsewhere, finer incremental movements are achieved. The movements approach zero at the shaft's rotational limits (0° and 180°). A small portion of the travel function curve of FIG. 4 is shown enlarged in FIG. 4A. As with all mechanical linkages, the linear motion is not a smooth function of shaft rotation but rather is subject to variations. This is acceptable as long as the variations are small relative to the desired motion. An unacceptably large variation of motion is shown in FIG. 4B. In the portion of the travel function curve between the lines 102 and 104 there is a reversal in direction. Some automatic focusing systems can become trapped in the valley between the two lines 102 and 104. For example, suppose it is desired to move the objective lens from the point marked 106 to the point marked 108 in order to obtain the correct focus. In making the incremental step between the point marked 110 and the point marked 112 such systems will sense that this step produced worse focusing and will supply a pulse to the stepping motor which moves the objective lens back from the point 112 to the point 110. The system is still not in correct focus and the elctronics will oscillate the objective lens between the points 110 and 112. This can be avoided by using the mechanism of this invention.

Such a mechanism is shown in FIG. 3. The stepping motor 50 is capable of 200 individual steps per revolution. It is mounted directly on the optical baseplate 114. The stepping motor has a vertical shaft 116 which extends through and beneath the baseplate 114. A worm gear 117 is directly connected to the shaft 116.

The worm gear 117 is in proper position for alignment with a worm wheel 118 which is attached to a shaft 115. The shaft 115 is at right angles to the motor shaft 116 and the shaft 115 extends in a front-to-rear direction underneath the optical baseplate from a position in front of the front brace 120 back through the front vertical plate 122.

The rotation of the shaft 115 in relation to the rotation of the motor shaft 116 is reduced by the worm and worm wheel by a ratio of 60 to 1.

A spring 128 has one end attached to shaft 115 and the other end attached to the front vertical plate 122. Several spirals of the spring are wound about the shaft to apply rotational torque to the shaft thereby eliminating any backlash between the mesh of the worm on the motor shaft and the worm wheel on the shaft 115.

The rear end of shaft 115 carries a cam 130 which activates two switches 132 in such a manner as to restrict the rotation of the shaft to 180°. The cam 130 and the switches 132 are arranged so that the eccentric member reaches its highest point of eccentric rotation as one limit is reached and its lowest point as the other limit is reached.

Machined onto the front of the shaft 115 is a smaller offset section 119. This portion is offset 0.010 inches from the centerline of the shaft 115. This forms an eccentric which moves up and down a total of 0.020 inches per 180° of revolution of the shaft 115. A precision ball bearing 134 is pressed lightly onto the offset shaft section. The offset shaft section extends through the hole in the front brace 120. The bearing 134 supports a protrusion 136 attached to the movable portion of the objective holder 138.

The objective holder 138 consists of a stationary unit 140 attached to the front brace 120 and a movable unit 142 which has a spring 144 which loads the protrusion 136 down on the eccentric bearing 134. This allows the assembly to (1) adjust vertically in response to rotation of the eccentric shaft, and (2) to lift free (approximately ⅛ inch) to the limitation of the spring.

An additional part 146 to which the objective is actually attached, is fitted snugly into a machined recess in the movable unit in such a manner as to allow the objective to be adjusted vertically approximately 0.100 inch up or down from design nominal position. Compensation for tolerance buildup in the assembly of the machine can be accomplished by loosening two screws 148 and 150. These screws firmly lock the two parts together after adjustment. Because this adjustment is one of the final assembly steps, a pin 152 positions these parts in their nominal design position until the balance of the machine has been assembled. This adjustment is used for "fine tuning" the relative positions of a 0.040 inch thick prepared slide resting properly on the stage of the completely assembled machine and the nominal design position of the objective.

The movable unit 142 is referenced to the stationary unit 140 by bearing balls 143 rolling upon precision rods 154. The movable unit 142 has parallel vertical grooves precisely machined and arranged to accept and retain two standard precision rods. Each of these rods is cut to the same length as the grooves. Each rod contacts the bottom of the groove for its full length and each presses against an opposite side of the groove thereby making contact along the full length of the side of the grooves. These grooves face the outside of the left and right sides of the movable unit 142. Opposing the two grooves, the stationary unit 140 also has two grooves precisely machined vertically into two forward extensions which enclose the movable unit. One groove is machined and assembled identically to the grooves previously described. The second groove is similar but it is machined sufficiently deeper to accept a plate 156 of rigid material such as tool steel which fits snugly into the groove and forms a false bottom to the groove. This plate is provided with a means of adjustment by set screws 158.

The units are assembled with bearing balls placed between and touching each of four rods in each pair of inner and outer grooves. The balls are vertically positioned by a retainer 160 made from a low-friction material, in this particular instance 0.050 thick beryllium copper. Retainer 160 has holes slightly larger than the bearing balls machined through on the proper locations. At assembly the false-bottom plate 156 is adjusted by means of set screws in the stationary unit, pressing the two rods in the groove against the bearing balls 143. The bearing balls in turn bear upon the rods on this side of the movable unit, causing the entire movable unit to move toward the opposite side until the rods in the groove on that side press the bearing balls on that side against the rods in the outer stationary unit on that side until a state of contact exists throughout. Adjustment is continued until all free play is eliminated, but is stopped before a rough, binding motion is developed.

The result is a well-controlled extremely low friction translatory motion.

In operation, a single step of the motor gives the motor shaft a worm 1/200 revolution, and through the 60:1 worm gear reduction, gives the eccentric shaft 1/12000 revolution, or a step of 0.03°. In the coarsest segment of the eccentric motion, this amounts to 0.0000052 inch per step. Since the depth of focus in this system is 1 micron or approximately 0.000040 inch, we have, in the worst condition, almost eight steps to achieve best focus. Since this is a nonlinear system and since few slides are exactly at design thickness of 0.040 inch, more steps are available as we approach the design limitations of 0.030 inches to 0.050 inch slide thickness (in either direction from nominal).

In summary, the focus mechanism permits the use of a stepping motor to actuate an eccentric bearing through an anti-backlash worm-and-worm gear arrangement, through a 180° arc providing ultra-small steps within a plus-or-minus 0.010 inch range to an adjustable objective which can be lifted free and cannot be driven into a slide, for the purpose of focusing such an objective within a 1 micron depth of field by means of external electronic feedback inputs to the stepping motor.

While a particular embodiment of the invention has been shown and described, it will, of course, be understood that various modifications may be made without departing from the principles of the invention. The appended claims are, therefore, intended to cover any such modification within the true spirit and scope of the invention.

What is claimed is:

1. An automatic focusing system for use in optics wherein it is desired to produce a focused image comprising:
    an adjustable objective lens producing said image,
    light sensing means responsive to the focus of said image producing electrical signals representing the direction of movement of said objective lens to produce focus, a stepping motor, said electrical signals being applied to said stepping motor, an eccentric member, said stepping motor being connected to rotate said eccentric member, a holder for said objective lens constrained for movement in a linear direction, and motion transmitting means connecting said eccentric member to said holder for moving said holder linearly as said stepping motor rotates.

2. The system recited in claim 1 wherein said motion transmitting means comprises a protrusion on said holder, said eccentric member bearing against said protrusion.

3. The system recited in claim 2 further comprising roller bearings constraining said holder for linear movement, and a roller bearing on said eccentric member, said roller bearings providing rolling interfaces for movement of said holder so that said stepping motor need overcome only rolling friction to move said holder.

4. The system recited in claim 3 further comprising a spring loaded worm gear drive between said stepping motor and said eccentric member to accurately rotate said eccentric member with no slip.

5. A system producing an electrical output representing the optical characteristics of an analytical slide comprising:

an adjustable objective lens producing an image of said slide, means for projecting the slide image to an actual image plane and to a parfocal image plane, conversion means positioned at a desired image plane which is coincident with said actual image plane when said slide image is in focus, said conversion means producing said electrical output representing the optical characteristics of said slide, first and second light sensing devices respectively receiving light from in front of said parfocal image plane, and behind said parfocal image plane, said light sensing devices respectively producing first and second electrical signals representing the position of said actual image plane with respect to said desired image plane, a stepping motor for moving said objective lens in either direction along the optical axis of said lens, a comparator for comparing the signals from said first and second light sensing devices, said comparator being connected to drive said stepping motor in a first direction when said first electrical signal is greater than said second electrical signal and in the opposite direction when said second electrical signal is greater than said first electrical signal, an eccentric member, said stepping motor being connected to rotate said eccentric member, and a holder for said objective lens constrained for movement in a linear direction, said eccentric member bearing against a protrusion on said holder to move said holder linearly as said stepping motor rotates.

6. The system recited in claim 5 further comprising: roller bearings constraining said holder for linear movement, and a roller bearing on said eccentric member, said roller bearings providing rolling interfaces for movement of said holder so that said stepping motor need overcome only rolling friction to move said holder.

7. The system recited in claim 5 further comprising: a spring loaded worm gear drive between said stepping motor and said eccentric member to accurately rotate said eccentric member with no slip.

8. A system producing an electrical output representing the optical characteristics of an analytical slide comprising:

an adjustable objective lens producing an image of said slide, conversion means positioned at a desired image plane which is coincident with the actual image plane when said slide image is in focus, said conversion means producing said electrical output representing the optical characteristics of said slide, first and second light sensing device respectively positioned to receive light from an image corresponding with the image in front of the desired image plane and behind the desired image plane, said light sensing devices producing first and second electrical signals, a differentiator, said electrical signals being applied to said differentiator to produce first and second differentiated electrical signals which represent the position of said image plane with respect to said desired image plane, a stepping motor, a comparator for comparing the signals from said differentiator, said comparator being connected to drive said stepping motor in a first direction when said first differentiated electrical signal is greater than said second differentiated electrical signal and in the opposite direction when said second differentiated electrical signal is greater then said first differentiated electrical signal, an eccentric member, said stepping motor being connected to rotate said eccentric member, and a holder for said objective lens constrained for movement in a linear direction, said eccentric member bearing against a protrusion on said holder to move said holder linearly as said stepping motor rotates.

9. The system recited in claim 8 further comprising: roller bearings constraining said holder for linear movement, and a roller bearing on said eccentric member, said roller bearings providing rolling interfaces for movement of said holder so that said stepping motor need overcome only friction to move said holder.

10. The system recited in claim 8 further comprising; a spring loaded worm gear drive between said stepping motor and said eccentric member to accurately rotate said eccentric member with no slip.

* * * * *